United States Patent [19]
Ohki et al.

[11] Patent Number: 5,715,811
[45] Date of Patent: Feb. 10, 1998

[54] INHALING TYPE MEDICINE ADMINISTERING DEVICE AND USING METHOD THEREFOR

[75] Inventors: Hisatomo Ohki, Isesaki; Atsuo Wakayama, Takasaki; Shigemi Nakamura, Isesaki; Kazunori Ishizeki, Fujimi; Akira Yanagawa, Yokohama, all of Japan

[73] Assignees: Unisia Jecs Corporation, Atsugi; Dott Limited Company, Yokohama, both of Japan

[21] Appl. No.: 537,862
[22] PCT Filed: May 25, 1995
[86] PCT No.: PCT/JP95/01007
§ 371 Date: Jan. 22, 1996
§ 102(e) Date: Jan. 22, 1996
[87] PCT Pub. No.: WO95/32751
PCT Pub. Date: Dec. 7, 1995

[30] Foreign Application Priority Data

May 26, 1994 [JP] Japan .................. 6-136420

[51] Int. Cl.⁶ .................................. A61M 15/00
[52] U.S. Cl. ............... 128/203.21; 428/203.15; 428/203.12
[58] Field of Search ............. 128/203.21, 203.15, 128/200.14, 203.12, 203.19, 203.23

[56] References Cited

U.S. PATENT DOCUMENTS

| | | | |
|---|---|---|---|
| 3,906,950 | 9/1975 | Cocozza | 128/203.21 |
| 3,971,377 | 7/1976 | Damani | 128/203.21 |
| 3,991,761 | 11/1976 | Cocozza | 128/203.21 |
| 4,884,565 | 12/1989 | Cocozza | 128/203.21 |
| 4,995,385 | 2/1991 | Valentini et al. | 128/203.21 |

FOREIGN PATENT DOCUMENTS

| | | |
|---|---|---|
| 653634 | 10/1994 | Australia . |
| 0 303 844 A1 | 2/1989 | European Pat. Off. . |
| 0 528 764 A1 | 2/1993 | European Pat. Off. . |
| 92 02 198.0 | 6/1992 | Germany . |
| WO 91/02558 | 3/1991 | WIPO . |
| WO 92/03175 | 3/1992 | WIPO . |

*Primary Examiner*—Vincent Millin
*Assistant Examiner*—William J. Deane, Jr.
*Attorney, Agent, or Firm*—Foley & Lardner

[57] ABSTRACT

An inhaling piece 1 is formed with an inhaling mouth 3 and a holder accommodating section 2. A capsule holder 6 is formed with a capsule accommodating hole 7 and air flow passages 8, 8 which extend axially, and is further formed with pin insertion holes 10, 11 which extend diametrically and are in communication with these air flow passages 8. When a capsule 17 is accommodated in the capsule accommodating hole 7 and the pins 16 are inserted into the pin insertion holes 10, 11, through-holes H, H, . . . are formed in the capsule 17. When the patient intends to inhale medicine, inhaling is made by first returning the pins 16 to the inhaling piece 1 so that the medicine can be securely and effectively carried to the lungs of the patient under the action of air flow.

13 Claims, 12 Drawing Sheets

INHALING TYPE MEDICINE ADMINISTERING DEVICE AND USING METHOD THEREFOR

FIELD OF THE INVENTION

This invention relates to an inhaling type medicine administering device, for example, suitable to be used for administering granular medicine into lungs under breathing-in action of a patient, and a using method thereof.

BACKGROUND OF THE INVENTION

Methods for administering medicine to the lungs of an asthma patient or the like, include injecting liquid medicine, causing the patient to inhale the medicine by using a liquid aerosol sprayer, allowing the patient to inhale fine granules (having a grain size of, for example, from 5 to 10 μm) filled in a capsule by breaking the capsule, and the like.

Of these medicine administering methods for the asthma patient, the method where the patient inhales the granular medicine filled in the capsule is carried out as follows: The asthma patient holds in his hand an inhaler through which the granular medicine is inhaled; installs the capsule in the inhaler; breaks the capsule with a perforating needle; and inhales the granular medicine through an inhaling opening, or mouthpiece.

However, the inhaler employed in a capsule type device according to a conventional technique is arranged such that only one or two holes are formed in the capsule, and therefore the shape of the hole is not constant, so that there arise problems in which the medicine cannot be sufficiently inhaled.

Additionally, depending on the shape and the area of the hole formed in the capsule, there arise problems in which a large amount of the granular medicine is left in the capsule, thereby causing lack of uniformity in ejection amount (amount of the patient) the medicine.

Further, there are problems in which, for example, the capsule unavoidably drops if the capsule is installed upside down in the inhaler, and it is difficult to take the capsule out of the inhaler after the capsule has been used since the structure of the inhaler is insufficient.

DISCLOSURE OF THE INVENTION

The present invention has been made in view of the above-mentioned problems encountered in the conventional technique and is intended to provide an inhaling type medicine administering device by which the entire amount of granular medicine in a capsule can be effectively administered into the lungs of a patient, and a using method therefor.

An inhaling type medicine administering device of the present invention comprises a medicine administering device main body having an end serving as a capsule accommodating hole and another end serving as an inhaling mouth, an air flow passage formed axially in the medicine administering device main body, a pair of pin insertion holes located on opposite sides of the above-mentioned capsule accommodating hole and formed diametrically in the above-mentioned medicine administering device main body so as to be respectively in communication with an inflow-side and an outflow-side of the air flow passage, and a perforator having pins which are arranged to be inserted through the respective pin insertion holes toward the capsule in order to form holes in the capsule when the capsule is located in the above-mentioned capsule accommodating hole.

Accordingly, first the capsule is positioned within the capsule accommodating hole of the medicine administering device main body, and subsequently the pins of the perforator are inserted respectively into two pin insertion holes. The holes formed in the medicine-filled capsule by the pins of the perforator are arranged to allow the inflow-side of the air flow passage to be in communication with the inside of the capsule through the pin insertion hole, and to allow the inside of the capsule to be in communication with the outflow-side of the air flow passage. Under this condition, when the patient inhales air through the inhaling mouth, air flows from the inflow-side of the air flow passage→the pin insertion hole→ the inflow-side hole in the capsule→the inside of the capsule→the outflow-side hole in the capsule→the pin insertion hole→the outflow-side of the air flow passage→the inhaling mouth, and flows to the lungs through the mouth, the trachea and the like of the patient. At this time, when air penetrates through the inflow-side hole in the capsule and is discharged through the outflow-side hole, the medicine filled in the capsule is spread and mixed in the discharging air, so that the medicine can be administered into the lungs of the patient under the action of air ejected from the inhaling type medicine administering device.

Air in the air flow passage is bifurcated into an inflow line of the inflow-side of the air flow passage→the pin insertion hole→the inside of the capsule and into an outflow line of the intermediate air flow passage→the outflow-side of the air flow passage through which line air flows out to the inhaling piece, so that a flow from the capsule is formed at a portion at which the flows are combined with each other, thereby making possible to disperse air from the capsule and thus making possible to readily carry the medicine within the capsule.

Additionally, a pair of the air flow passages communicating with the respective pin insertion holes are formed diametrically opposite to each other. As a result, when air flowing through the respective air flow passages penetrate into the capsule, air flows in through the diametrically located pin insertions holes, so that air flows from the diametrically opposite sides collide with each other within the capsule, thereby causing the granular medicine to be mixed into air.

Further, the medicine administering device main body comprises the inhaling piece and the capsule holder which are arranged to be detachable, and therefore it is possible to readily remove pieces produced during formation of the holes in the capsule and the adhered medicine.

Furthermore, the air flow passage is reduced in diameter at its portion between the inflow-side pin insertion hole and the outflow-side pin insertion hole, and therefore air flowing from the one end to the other end of the air flow passage can be preferentially guided through the pin insertion hole into the capsule, and the flow speed of air during flowing from the inflow-side to the outflow-side is raised, so that such air is combined with the medicine sucked out through the outflow-side pin insertion hole, thereby improving a discharging effect.

The capsule is positioned within the capsule accommodating hole of the medicine administering device main body, and subsequently the pins of the perforator are inserted respectively into two pin insertion holes. The holes formed in the medicine-filled capsule by the pins of the perforator are arranged to allow the inflow-side of the air flow passage to be in communication with the inside of the capsule through the pin insertion hole, and to allow the inside of the capsule to be in communication with the outflow-side of the 
air flow passage. Under this condition, when the patient inhales air through the inhaling mouth, air flows through the inflow-side air flow passage→the pin insertion hole→the inflow-side hole in the capsule→the inside of the capsule→the outflow-side hole in the capsule→the pin insertion hole→the outflow-side air flow passage→the inhaling mouth, and flows to the lungs through the mouth, the trachea and the like of the patient. At this time, when air penetrates through the inflow-side hole in the capsule and is discharged through the outflow-side hole, the medicine filled in the capsule is spread and mixed in the discharging air, so that the medicine can be administered into the lungs of the patient under the action of air ejected from the inhaling type medicine administering device.

Figure 4:
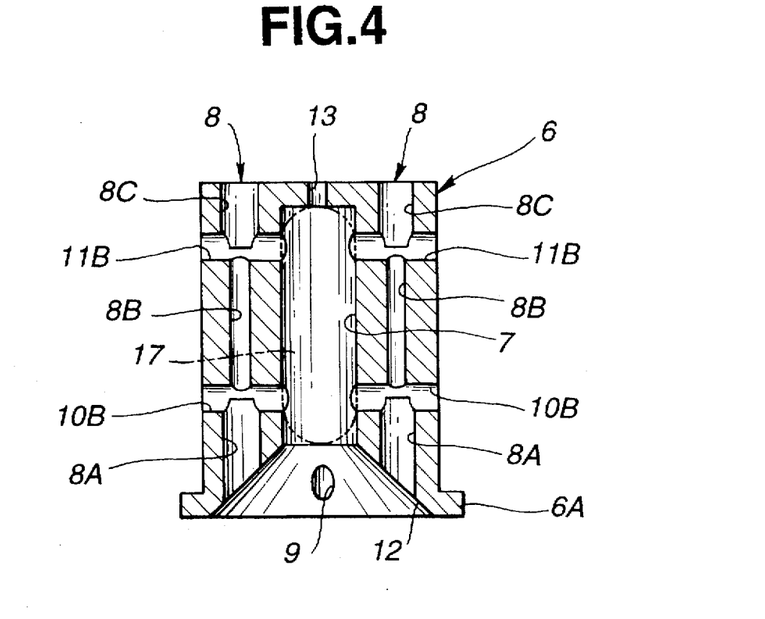
Figure 5:
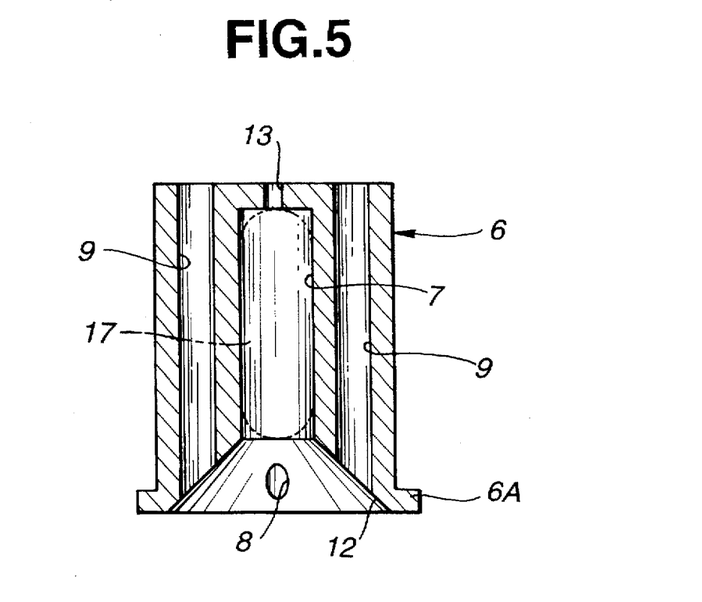
Figure 6:
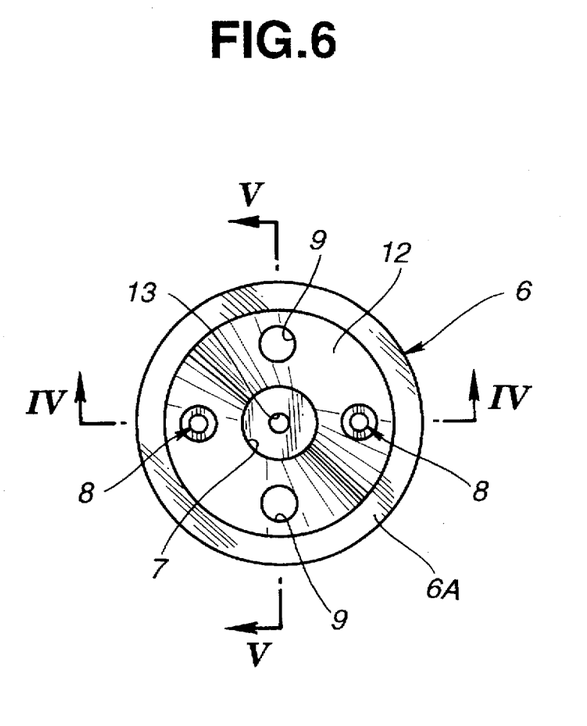

Air flown in through the air flow passage flows in a line of the inflow-side air flow passage→the pin insertion hole→the outflow-side air flow passage inside the capsule, and therefore whole of inhaled air from the inflow-side air flow passage can be flown to the outflow-side air flow passage so that the medicine within the capsule can be readily carried even under a weak sucking force. Additionally, the inflow-side air flow passage and the outflow-side air flow passage which are respectively in communication with the respective pin insertion holes are formed diametrically opposite to each other. Accordingly, when air penetrates into the capsule from each inflow-side air flow passage, air flows in through the diametrically located pin insertion holes, so that respective air flows from the diametrically opposite sides collide with each other within the capsule and are spread, thereby causing the granular medicine to be mixed in air. This spread air is discharged through the air outflow-side air flow passage.

Further, by providing an auxiliary air flow passage, the patient can strongly inhale air, thereby making air inhaling easy.

Additionally, by inserting a needle in a small diameter hole, the capsule can be readily extracted from the capsule accommodating hole.

Furthermore, a method of using this inhaling type medicine administering device comprises inserting a capsule holder in the holder accommodating section of the above-mentioned inhaling piece, aligning outside pin insertion holes formed in the above-mentioned inhaling piece respectively with inside pin insertion holes formed in the capsule holder so as to constitute an inflow-side pin insertion hole and an outflow-side pin insertion hole, inserting the pins of the perforator respectively through the pin insertion holes from a side surface of the inhaling piece under this condition so as to form through-holes in the capsule, and thereafter drawing out the above-mentioned perforator to a position at which a tip end section of each pin is positioned in the above-mentioned outside pin insertion hole. This completes the preparation for inhaling the medicine. Accordingly, the inhaling type medicine administering device may be simply and readily used by the patient so that the medicine administering device is high in practicality.

BRIEF DESCRIPTION OF DRAWINGS

FIG. 1 is an exploded perspective view showing an inhaling type medicine administering device according to a first embodiment;

FIG. 2 is a vertical sectional view showing an inhaling piece in FIG. 1;

FIG. 3 is a bottom view of the inhaling piece as viewed from the bottom face side;

FIG. 4 is a vertical sectional view of a capsule holder, taken in the direction of arrows along the line IV—IV of FIG. 6;

FIG. 5 is a vertical sectional view of the capsule holder, taken in the direction of arrows along the line V—V of FIG. 6;

FIG. 6 is a bottom view of the capsule holder, as viewed from the bottom face side;

FIG. 7 is a vertical sectional view showing a state in which capsule is to be positioned in a capsule accommodating hole of the capsule holder;

FIG. 8 is a vertical sectional view showing a state in which the pins of a perforator are inserted into pin insertion holes after the capsule has been positioned in the capsule accommodating hole;

FIG. 9 is a vertical sectional view showing a state in which holes have been formed by inserting the pins into the pin insertion holes;

FIG. 10 is an enlarged vertical sectional view showing flow of air generated during inhaling;

FIG. 11 is a vertical sectional view of the inhaling type medicine administering device according to a second embodiment, showing a state in which the perforator has been removed;

FIG. 12 is a vertical sectional view showing the capsule holder in FIG. 11; and FIG. 13 is an enlarged vertical sectional view showing flow of air generated during inhaling.

DETAILED DESCRIPTION OF THE INVENTION

Hereinafter, embodiments of the present invention will be discussed in detail with reference to FIGS. 1 to 13.

FIGS. 1 to 10 show a first embodiment of the present invention. An inhaling piece 1 comprises part of the main body of a medicine administering device and is cylindrically formed of a material designated by the Drugs, Cosmetics and Medical Instruments Act. As shown in FIGS. 2 and 3, the inhaling piece 1 includes at its one end side (inflow side) a holder accommodating section 2 which is thick to keep therein a capsule holder 6 which will be discussed after, an inhaling mouth or mouthpiece 3 which tapers toward the other end side (outflow-side) of the inhaling piece 1, and a flange section 4 located between the inhaling mouth 3 and the holder accommodating section 2 and formed at the outer peripheral side thereof, in which the inhaling mouth 3 is formed at its inner diameter side with an outflow passage 5. Additionally, the above-mentioned holder accommodating section 2 is formed with first pin insertion holes 10A, 11A which are formed axially separate from each other and only at a diametrical one side which holes 10A, 11A constitute respectively parts of pin insertion holes 10, 11 which will be discussed after. A circular depression 2A is formed between the first pin insertion holes 10A, 11A.

A capsule holder 6 in combination the inhaling piece 1 comprise the medicine administering device main body. The capsule holder 6 is columnar and formed at its one end face with an annular stopper section 6A by which the capsule holder 6 is positioned in the capsule accommodating section 2.

Here, the inside structure of the above-mentioned capsule holder 6 will be explained with reference to FIGS. 4 to 6.

A capsule accommodating hole 7 is located at the central section of, and extends axially in, the capsule holder 6. The capsule accommodating hole 7 is arranged such that a capsule 17, which will be discussed after, is to be inserted into the capsule accommodating hole from the opened one end side of the capsule accommodating hole.

Two air flow passages 8, 8 axially pierce the capsule holder 6. The respective air flow passages 8 are diametrically opposite to each other, as shown in FIG. 4. Additionally, the air flow passages 8, 8 are in communication with the pin insertion holes 10, 11, which will be discussed after. Each air flow passage 8, 8 includes a large diameter inflow-side air flow passage 8A which extends from its one end to a position communicating with the inflow-side pin insertion hole 10, a small diameter orifice passage 8B which extends between the inflow-side pin insertion hole 10 and a position communicating with the outflow-side pin insertion hole 11, and a large diameter outflow-side air flow passage 8C which extends from the outflow-side pin insertion hole 11 to the other end of the airflow passages.

Two auxiliary air passages 9 axially pierce the capsule holder 6 at positions which shift by an angle of 90 degrees from the respective air flow passages 8. Each auxiliary air flow passage 9 has the same diameter throughout its length and axially extends from one end to the other end of the capsule holder 6.

The inflow-side pin insertion hole 10 and the outflow-side pin insertion hole 11 are located at the axially opposite sides of the capsule accommodating hole 7 and located to pierce, respectively, the two inflow-side portions and two outflow-side portions of the air flow passages 8. Each pin insertion hole 10 (11) includes the outside pin insertion hole 10A (11A) formed at the diametrical-direction side of the holder accommodating section 2 of the inhaling piece 1, and the inside pin insertion holes 10B, 10B (11B, 11B) which are in communication with the outside pin insertion hole 10A (11A) and formed straight to extend diametrically through the capsule accommodating hole 7 of the above-mentioned capsule holder 6.

A tapered surface 12 is formed at one end face of the capsule holder 6. A small diameter hole 13 is formed at the center of the other end face of the capsule holder 6 and is in communication with the above-mentioned capsule accommodating hole 7.

Figure 1:
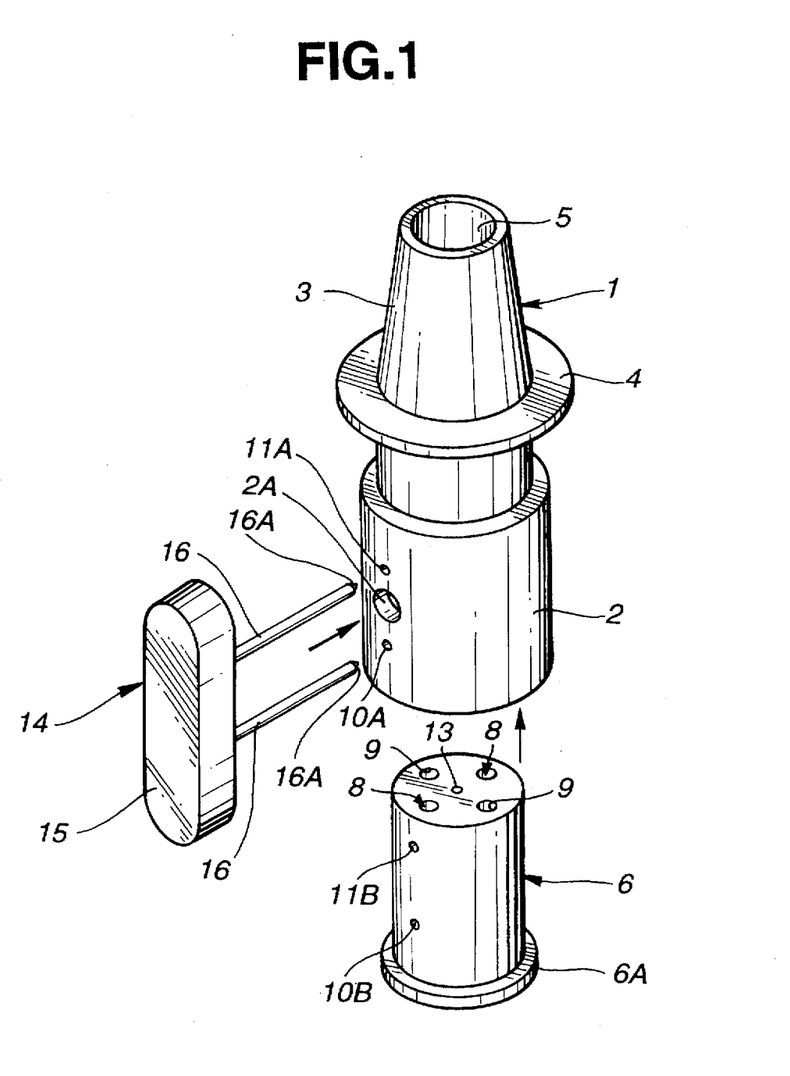
Figure 2:
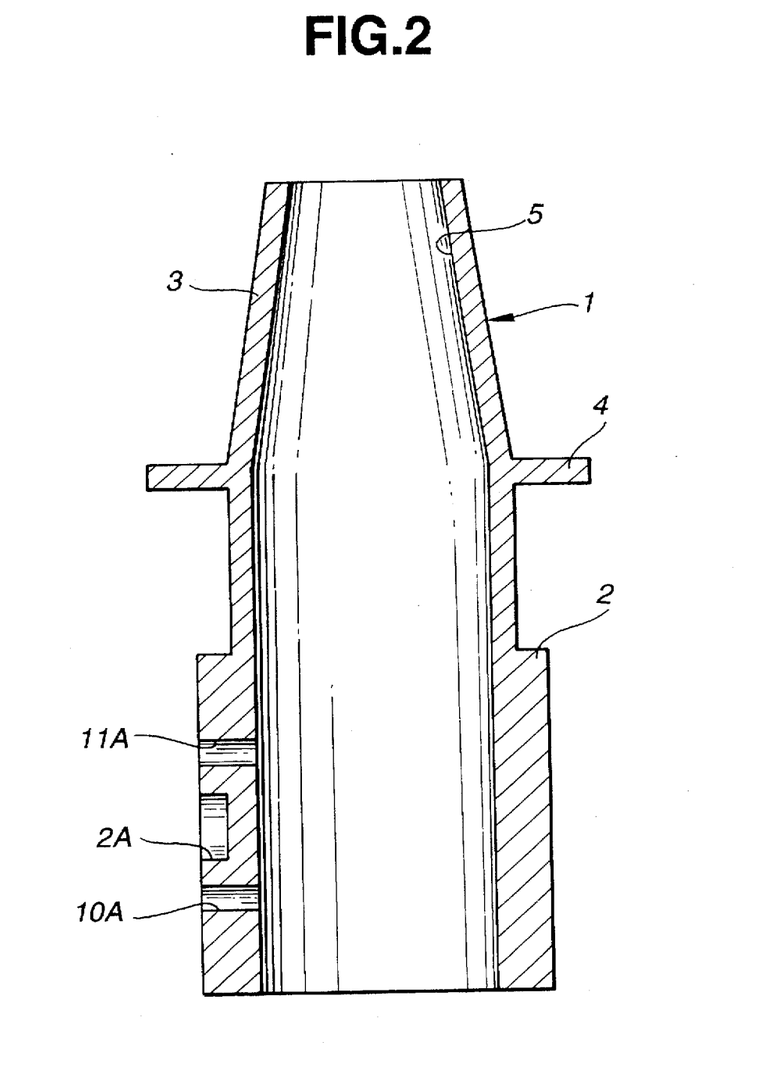
Figure 3:
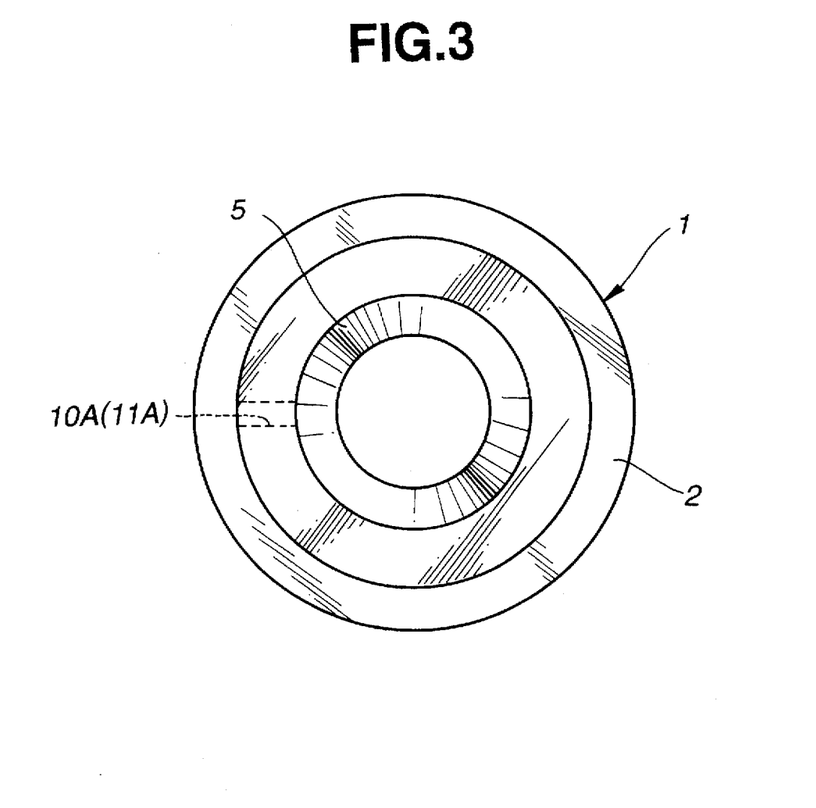
Figure 9:
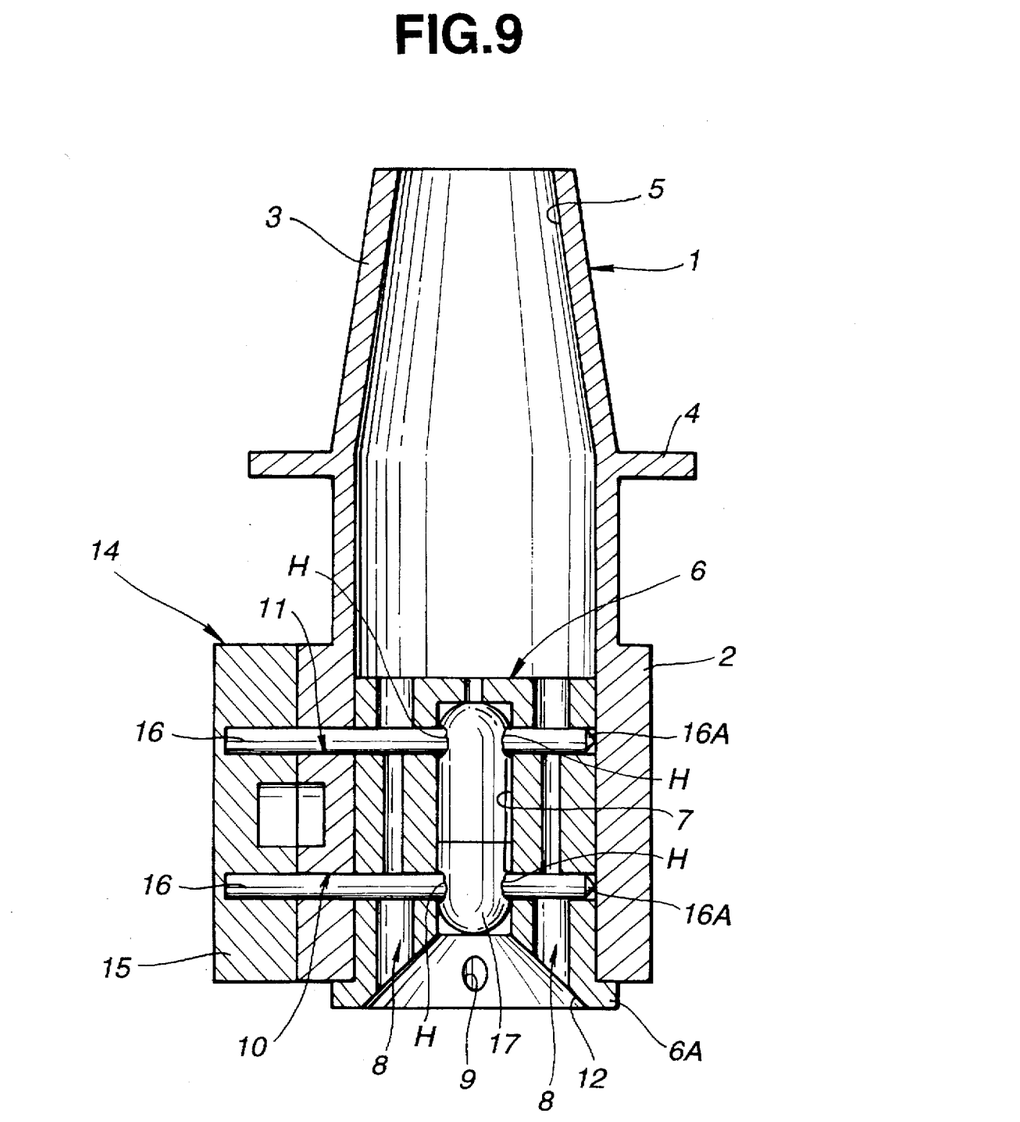

A perforator 14 for forming holes in the capsule 17 is shown in FIG. 1. The perforator 14 includes a support section 15 and pins 16, 16 which project from the support section 15. The pins 16, 16 are separate from each other by a distance dimension same as that between the above-mentioned respective pin insertion holes 10, 11, the tip end of each pin being formed as a conical hole formation section 16A. Additionally, when each pin 16, 16 is inserted into the above-mentioned pin insertion hole 10, 11, its hole formation section 16A passes through the outside pin insertion hole 10A, 11A→the inside pin insertion hole 10B, 11B→the capsule accommodating hole 7→the inside pin insertion hole 10B, 11B and comes into contact with the inside surface of the holder accommodating section 2. As shown in FIG. 9, when each hole formation section 16A passes through the capsule 17 in the capsule accommodating hole 7, through-holes H, H, . . . are formed in the capsule 17 without breaking the capsule 17.

Further, the capsule 17 is in the shape of a long cylinder and may be filled with granular medicine.

The above-mentioned support section 15 is formed with a circular depression 15A which is located at a position opposite the depression 2A formed in the above-mentioned holder accommodating section 2.

The inhaling type medicine administering device of this embodiment is arranged as discussed above. Preparation up to the time at which the patient inhales the medicine, now will be discussed along with air flow within the inhaling type medicine administering device during inhaling, with reference to FIGS. 7 to 10.

First, the capsule holder 6 is inserted into the holder accommodating section 2 of the inhaling piece 1 through one end side of the holder accommodating section 2, and inserted until the stopper section 6A of the capsule holder 6 comes into contact with the one end side of the holder accommodating section 2. The outside pin insertion holes 10A, 11A formed in the inhaling piece 1 are respectively aligned with the inside pin insertion holes 10B, 11B formed in the capsule holder 6 so as to form the inflow-side pin insertion hole 10 located at the one end side and the outflow-side pin insertion hole 11 located at the other end side.

Figure 7:
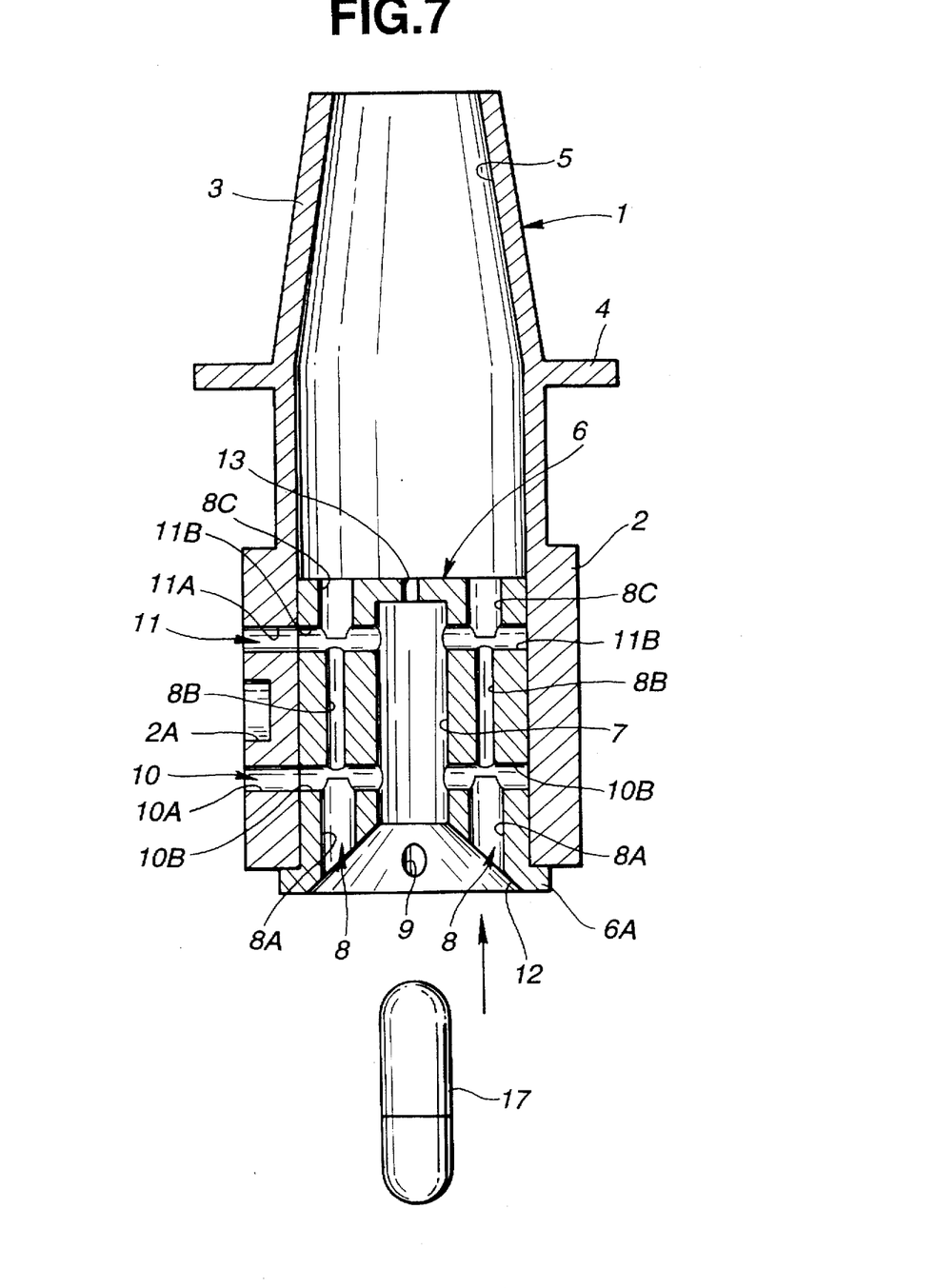

As shown in FIG. 7, the capsule 17 is inserted into the capsule accommodating hole 7 through one end of the hole 7 to be positioned and accommodated in the hole 7. An end face of the capsule holder 6 is formed into a tapered surface 12, and therefore the capsule 17 can be readily guided into the capsule accommodating hole 7.

Figure 8:
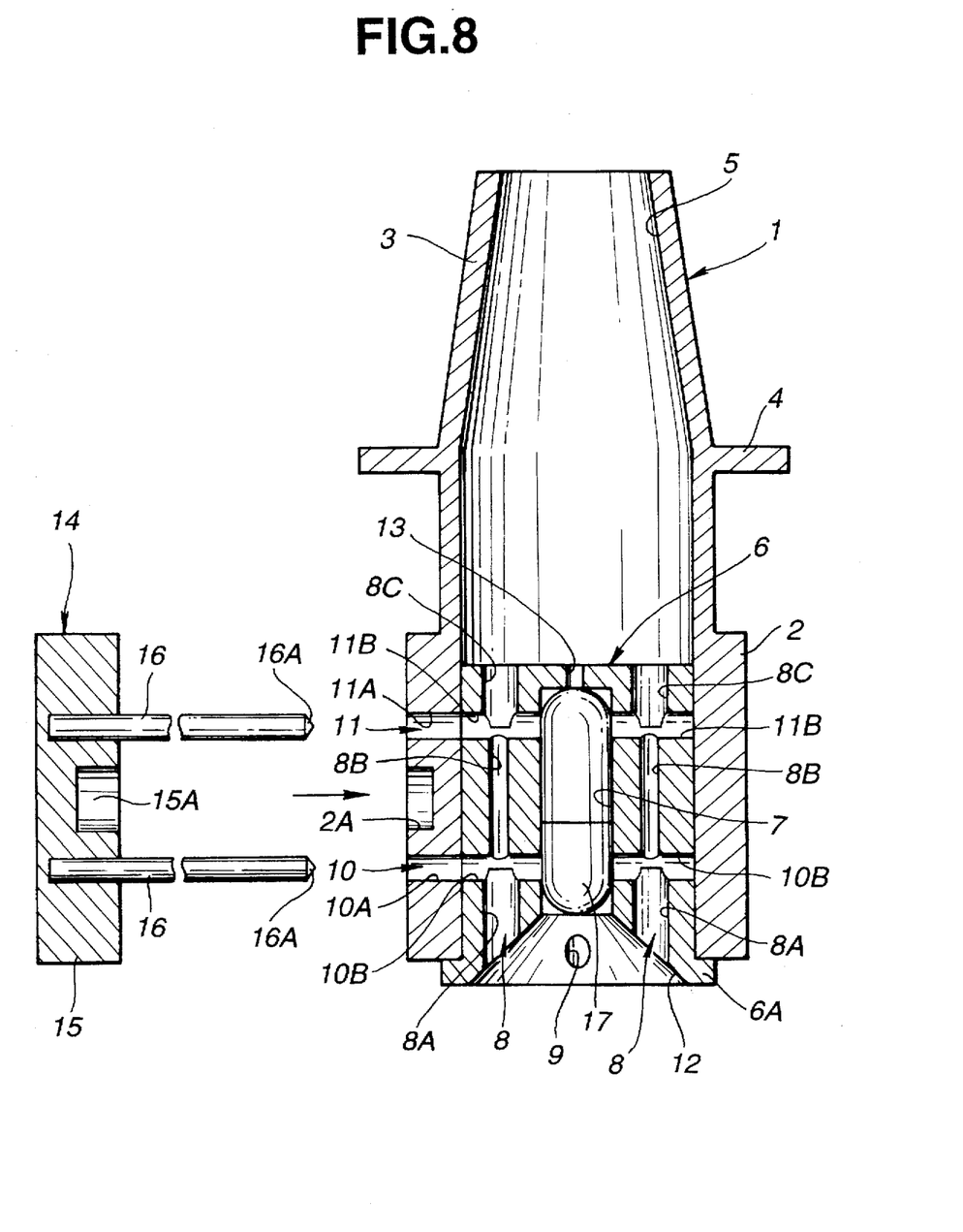

Further, when the capsule 17 has been accommodated in the capsule accommodating hole 7 as shown in FIG. 8, the pins 16 of the perforator 14 are respectively inserted into the pin insertion holes 10, 11 from the side surface of the inhaling piece 1.

Then, the hole formation section 16A of each pin 16 is passed through the outside pin insertion hole 10A, 11A→the inside pin insertion hole 10B, 11B→the capsule accommodating hole 7→the inside pin insertion hole 10B, 11B, and comes into contact with the inside surface of the holder accommodating section 2 (See FIG. 9). At this time, when each hole formation section 16A passes through the capsule accommodating hole 7, four through-holes H, H, . . . are securely formed in the capsule 17 accommodated in the capsule accommodating hole 7.

Figure 10:
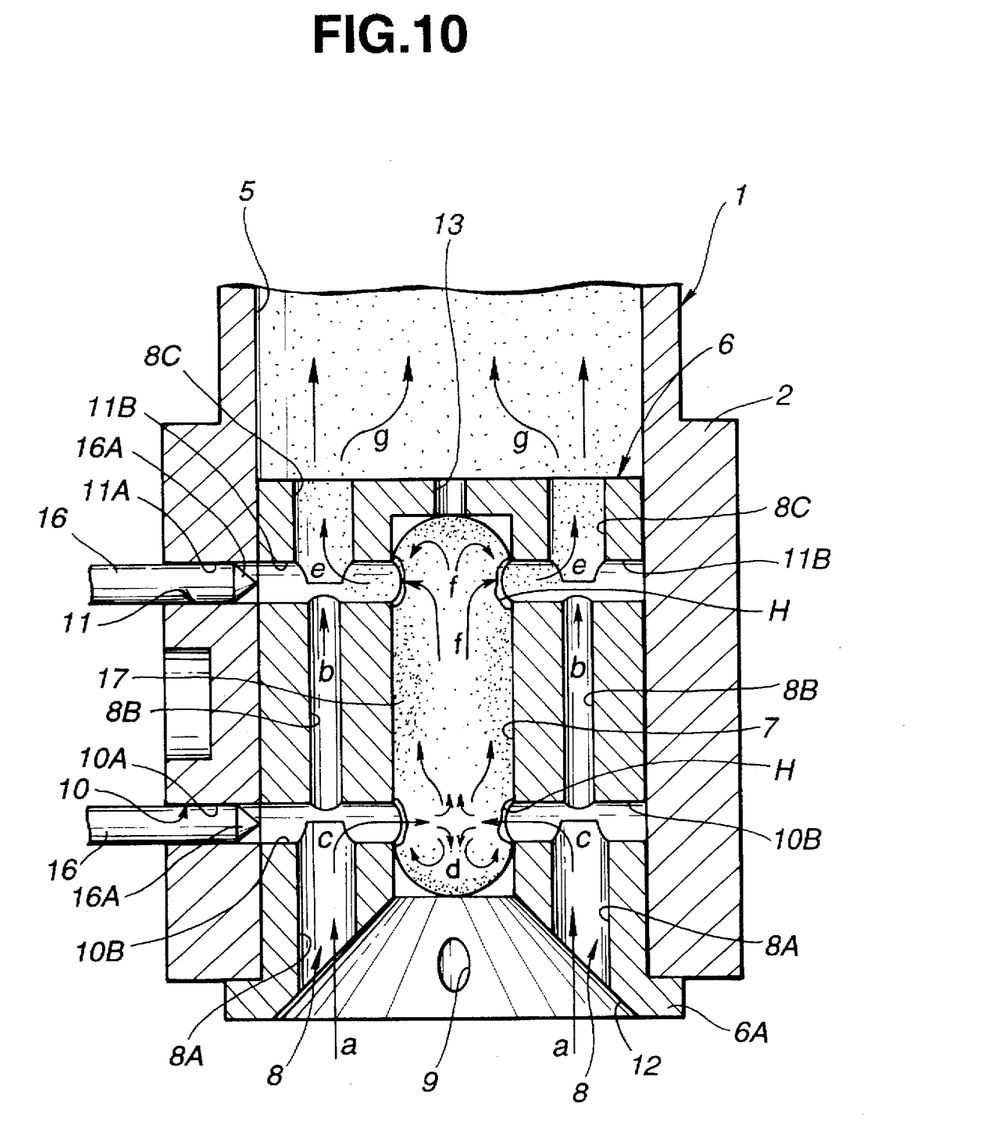

After the four through-holes H have been thus formed in the capsule 17, each pin 16 is returned to its position at which its hole formation section 16A is positioned within the outside pin insertion hole 10A, 11A as shown in FIG. 10 when the patient inhales the medicine.

Next, air flow within the inhaling type medicine administering device will discussed, along with movement of the medicine during a time in which the patient inhales the medicine, with reference to FIG. 10.

First, when the patient holds the inhaling mouth 3 in the patient's mouth and breathes in, air flows into the inhaling type medicine administering device through the respective air flow passages 8, 9. Then, the flow of the air in the auxiliary air flow passages 9, 9 not shown in FIG. 10 flows from their one end to the other end and flows into the outflow passage 5.

Additionally, in the air flow passages 8, 8 shown in FIG. 10, air is sucked from the inflow-side air flow passages 8A, 8A as indicated by arrows a, a. This air is bifurcated into the small diameter orifice passage 8B, 8B and into the inside pin insertion hole 10B, 10B as indicated by arrows b, b and arrows c, c. Air which preferentially flows from the large diameter inflow-side air flow passage 8A, 8A as indicated by the arrows c, c flows into the capsule accommodating hole 7 through each inside pin insertion hole 10B. Since the through-holes H, H have been already formed in the capsule 17, air penetrates into the capsule 17 through the through-holes H.

At this time, the respective inside pin insertion holes 10B are formed opposite to each other, and therefore air penetrating in the capsule 17 and indicated by the arrows c, c collide with each other, thereby generating turbulence indicated by arrows d, d within the capsule 17. Under the action of this flow indicated by the arrows d, d, the granular medicine is compulsorily spread, thereby causing the medicine to be securely mixed in air.

Concerning flow indicated by arrows e, e and flowing out of the capsule 17, the amount of flow penetrating into the capsule 17 as indicated by the arrow c constitutes the flow discharged from the capsule 17, thereby improving a discharge effect. Additionally, under the action of the flow of air which flows through the orifice air flow passage 8B, 8B as indicated by the arrows b, b upon being diverged from the above-mentioned flow indicated by the arrow c, flow (indicated by arrows e, e) is compulsorily generated in the inside pin insertion hole 11B, 11B and the outflow-side air flow passage 8C, 8C.

Since the medicine has been mixed in air of flow indicated by arrows f, f within the capsule 17, the medicine within the capsule 17 is dispersed by flow indicated by the arrows e, e and reaches through the inhaling mouth 3 to the inside of the mouth of the patient, and then reaches through the trachea to the lungs of the patient under the action of flow indicated by arrows g, g, . . . in the outflow passage 5, thus making it possible to securely administer the medicine mixed in air into the lungs.

Thus, in the inhaling type medicine administering device according to this embodiment, since the pin insertion holes 10, 11 are located at the opposite end sides of the capsule accommodating hole 7, the through-holes H, H, . . . can be securely formed in the capsule 17 with the hole formation section 16A of each pin 16 by inserting the pin 16, 16 into the pin insertion hole 10, 11.

Additionally, air in the air flow passage 8, 8 flows through the inflow-side pin insertion hole 10 and the through-holes H into the capsule 17, and makes it possible to cause air mixed with the medicine within the capsule 17 to be sprayed from the inhaling mouth 3 through the outflow-side pin insertion hole 11 and the air flow passage 8, 8, thereby making it possible to cause the medicine in the capsule 17 to be administered into the lungs of the patient. As a result, administering the medicine to the patient can be effectively accomplished.

Further, the inside pin insertion holes 10B, 10B of the inflow-side pin insertion hole 10 are formed along a straight line so that air flows penetrating into the capsule 17 through the inside pin insertion holes 10B, 10B, of air flows from the inflow-side air flow passages 8A, 8A collide with each other. Under this collision, turbulence is generated within the capsule 17, thereby spreading the medicine in the capsule 17 thus effectively mixing the medicine in air. By this, the medicine in the capsule 17 can be effectively released from the inhaling mouth 3.

Furthermore, since each air flow passage 8 includes the small diameter air flow passage 8B, 8B which diverges from the inflow-side pin insertion hole 10 and from the outflow-side pin insertion hole 11, a large amount of air can be preferentially flown to each inside pin insertion hole 10B by virtue of each orifice air flow passage 8B, and additionally flow of air flowing from each inside pin insertion hole 11B to each outflow-side air flow passage 8C is formed, thereby making possible to securely spray air mixed with the medicine.

The medicine administering device main body according to this embodiment is constituted of the inhaling piece 1 and the capsule holder 6 which are arranged to be detachable, and therefore it is possible to easily accomplish cleaning to remove pieces produced during formation of each through-hole H in the capsule 17 and the adhered medicine by disassembling the main body. Additionally, the capsule 17 can be easily extracted by inserting a needle into the small diameter hole 13.

Additionally, by providing the auxiliary air flow passages 9, 9 separate from the air flow passages 8, 8 through which air mixed with the medicine flows, the patient can strongly inhale a large amount of air as compared with a case of inhaling air through a narrow air flow passage, thereby facilitating inhaling of air and reducing a patient's burden to inhale air.

Figure 11:
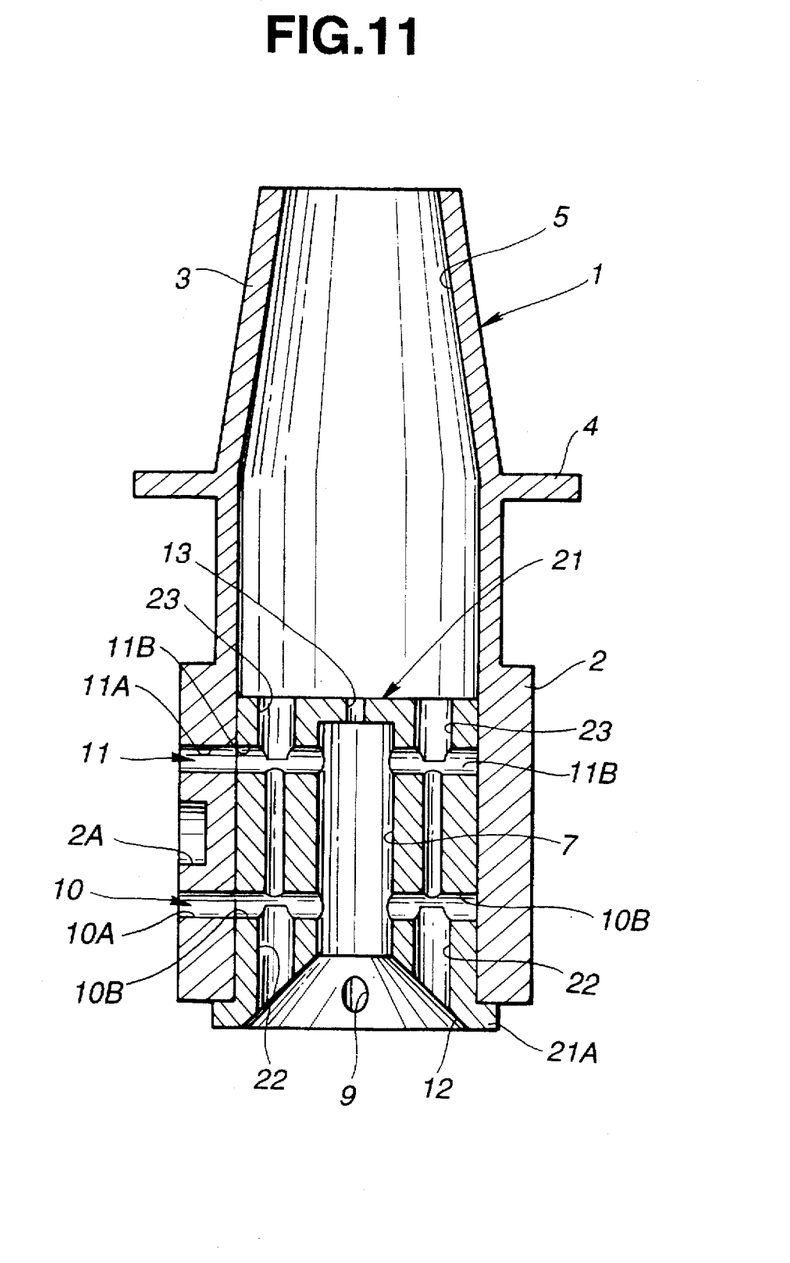
Figure 12:
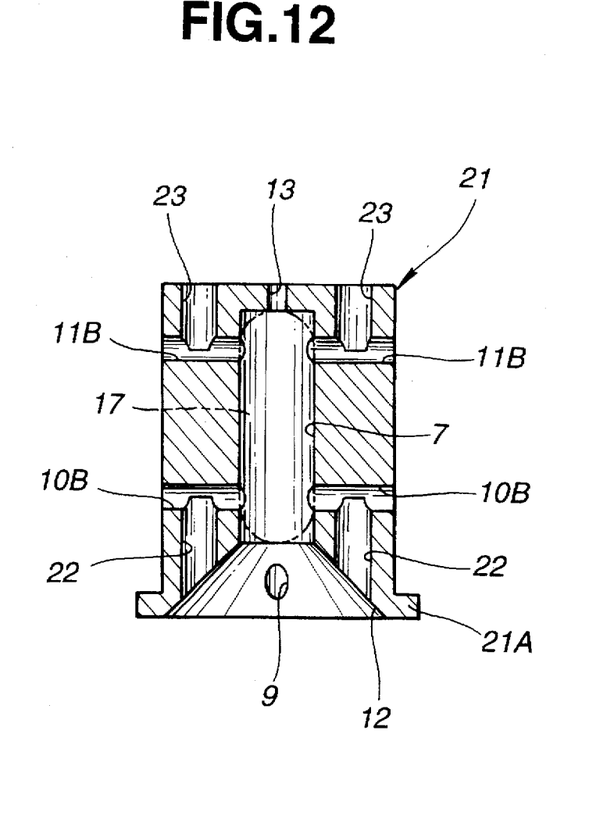
Figure 13:
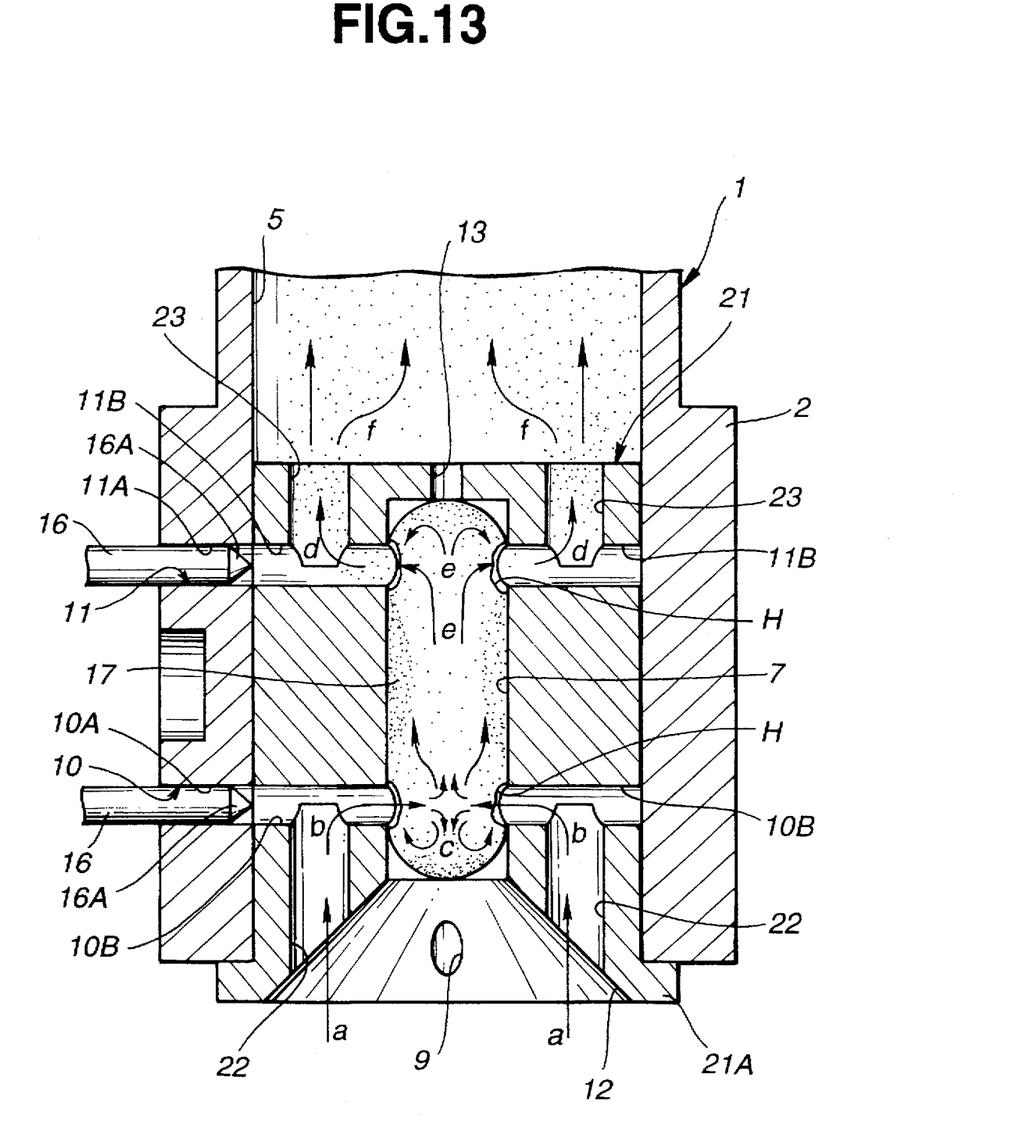

Next, a second embodiment according to the present invention is illustrated in FIGS. 11 to 13. The feature of this embodiment resides in cancelling the small diameter orifice air flow passages 8B, 8B located at the intermediate sections (between the pin insertion holes 10, 11) of the air flow passages 8, 8 formed in the axial direction of the capsule holder 6 in the first embodiment. The same reference numerals are assigned to the same constituting elements in the above-mentioned first embodiment in order to omit their explanation.

The capsule holder 21 is applied to this embodiment in place of the capsule holder used in the first embodiment. The capsule holder 21 is formed with the capsule accommodating hole 7, the inside pine insertion holes 10B, 11B, 10B, 11B, and the like as same as the capsule holder 6 in the first embodiment, in which the same reference numerals are assigned to the same constituting elements in order to omit their explanation.

Thus, in the capsule holder 21 of this embodiment, a pair of inflow-side air flow passages 22, 22 are located diametrically opposite to each other, and a pair of outflow-side air flow passages 23, 23 are located diametrically opposite to each other, in place of a pair of the air flow passages 8, 8 discussed in the first embodiment. Each inflow-side air flow passage 22 is in communication with each inside pin insertion hole 10B, while each outflow-side air flow passage 23 is in communication with each inside pin insertion hole 11B.

In other words, each air flow passage 8 in the first embodiment is constituted of the inflow-side air flow passage 8A, the orifice air flow passage 8B and the outflow-side air flow passage 8C. However, in this embodiment, the inflow-side air flow passages 22, 22 are communicated with the capsule accommodating hole through the respective inflow-side inside pin insertion holes 10B, while the outflow-side air flow passages 23, 23 are communicated with the capsule accommodating hole 7 through the respective outflow-side inside pin insertion holes 11B. Thus, in this embodiment, the orifice air flow passages 8B in the first embodiment are omitted. The capsule holder 21 is formed at its one end face with a stopper section 21A.

Also with the thus arranged inhaling type medicine administering device of this embodiment, administering the medicine to the patient can be easily accomplished similarly to that in the first embodiment.

In the inhaling type medicine administering device of this embodiment, the inflow-side air flow passage 22 and the outflow-side air flow passage 23, which are not communicated with each other in axial direction, are formed in place of the air flow passages 8, 8 in the first embodiment, and therefore air flow and movement of the medicine within the inhaling type medicine administering device at the time when the patient inhales the medicine are as shown in FIG. 13.

In other words, when the patient holds the inhaling mouth 3 in the patient's mouth and breathes in, air flows into the inhaling type medicine administering device through the respective air flow passages 22 and the respective auxiliary air flow passages 9. Then, the flow of the air in each auxiliary air flow passage 9 flows from its one end to the other end and flows into the outflow passage 5.

Additionally, in air flow in the inflow-side air flow passages 22, 22, air is sucked from the inflow-side air flow passages 22, 22 as indicated by arrows a, a. This air flows through the inflow-side inside pin insertion holes 10B, 10B in the directions indicated by arrows b, b and flows into the capsule accommodating hole 7. Since the through-holes H, H have been already formed in the capsule 17, air penetrates into the capsule 17 through the through-holes H.

At this time, since the respective inside pin insertion holes 10B are formed opposite to each other, air penetrating in the capsule 17 as indicated by the arrows b, b collide with each other thereby generating turbulence indicated by arrows c, c within the capsule 17. Under the action of this flow indicated by the arrows c, c, the granular medicine is compulsorily spread, thereby causing the medicine to be securely mixed in air.

Concerning flow indicated by arrows d, d and flowing out of the capsule 17, the amount of flow penetrating into the capsule 17 as indicated by the arrow b constitutes the flow discharged from the capsule 17, thereby generating the flow (indicated by arrows d, d) through the inside pin insertion holes 11B, 11B and the outflow side air flow passage 23, 23.

Since the medicine has been mixed in air of flow indicated by arrows e, e within the capsule 17, the medicine within the capsule 17 reaches through the inhaling mouth 3 of the patient and reaches through the inside of the mouth, the trachea into the lungs of the patient under the action of flow indicated by arrows d, d and indicated by arrows f, f, ... in the outflow passage 5, thus making it possible to securely administer the medicine mixed in air into the lungs.

Thus, in the inhaling type medicine administering device of this embodiment, whole inhaled air can be flown into the capsule accommodating hole 7 through the inflow-side air flow passage 22 and the inside pin insertion hole 10B, while air within the capsule accommodating hole 7 can be discharged through the inside pin insertion hole 11B and the outflow side air flow passage 23. By this, air can be flown through the capsule 17 so that the medicine in the capsule 17 is mixed in air and carried into the lungs, thereby securely administering the medicine even by a child or old person who is weak in sucking force.

In the above-mentioned respective embodiments, although the above embodiments include two air flow passages 8 (the inflow-side air flow passages 22 and the outflow-side air flow passages 23) for releasing the medicine and two auxiliary air flow passages 9 the number of air flow passages (23, 24) for allowing the medicine to flow and the number of auxiliary air flow passages may not be limited to two and may be adjusted as one, four, or the like in the present invention. The auxiliary air flow passage 9 may be omitted.

Additionally, although the medicine administering device main body comprises the inhaling piece 1 and the holder 6 (21) are detachable in the above-discussed respective embodiments, the inhaling piece 1 and the capsule holder 6 (21) alternatively 14 may be formed integrally with each other.

As discussed in detail above, according to the present invention, the holes formed in the capsule filled with the medicine by the pins of the perforator are arranged to allow the inflow-side of the air flow passage to be in communication with the inside of the capsule through the pin insertion hole, and to allow the inside of the capsule to be in communication with the outflow-side of the air flow passage. Under this condition, when the patient inhales air through the inhaling mouth, the stream of air flows through the inflow-side of each air flow passage→the inflow-side pin insertion hole→the inflow-side hole in the capsule→the inside of the capsule→the outflow-side hole in the capsule→the outflow-side pin insertion hole→the outflow-side of the air flow passage→the inhaling mouth, and flows to the lungs through the mouth, the trachea and the like of the patient. At this time, when air penetrates through the inflow-side holes in the capsule and is discharged through the outflow-side holes, the medicine filled in the capsule is spread by the flow of this air, so that the medicine can be carried upon being mixed in air released from the inhaling mouth, thereby effectively administering the medicine in the capsule into the lungs of the patient thus making it possible to securely improve the administering of the medicine.

Air in the air flow passage is bifurcated into an inflow line of the inflow-side of the air flow passage→the pin insertion hole→the inside of the capsule and into an outflow line of the intermediate air flow passage→the outflow-side of the air flow passage through which line air flows out to the inhaling piece, so that a flow from the capsule is formed at a portion at which the flows are combined with each other, thereby dispersing and securely carrying the medicine within the capsule.

Additionally, a pair of the air flow passages communicating with the respective pin insertion holes are formed diametrically opposite to each other. As a result, when air flowing through the respective air flow passages and the pin insertion holes penetrate into the capsule, air flows into the capsule from diametrically opposite sides of the capsule and collide with each other within the capsule, thereby forming turbulence and securely spreading the medicine. By this, the medicine spread in air can be effectively mixed, so that a large amount of the medicine can be mixed in air released from the capsule, thereby more effectively accomplishing administration of the medicine to the patient.

Further, the medicine administering device main body comprises the inhaling piece and the capsule holder which are arranged to be detachable, and therefore it is possible to remove pieces produced during formation of the holes in the capsule and the adhered medicine, thereby facilitating the cleaning of the inhaling type medicine administering device.

Furthermore, the air flow passage is reduced in diameter at its portion between the inflow-side pin insertion hole and the outflow-side pin insertion hole, and therefore air flowing from the one end to the other end of the air flow passage can be preferentially guided through the pin insertion hole into the capsule. As a result, air flow such as turbulence and the like generated in the capsule is made large, thereby making it possible to enlarge the amount of the medicine contained in air and effectively accomplishing administering the medicine into the lungs of the patient.

As discussed above, the inhaling type medicine administering device according to the present invention and its method of use can be applied to one in which fine granules or the like filled in a capsule are inhaled upon breaking the capsule.

We claim:

1. An inhaling type medicine administering device comprising:
   a main body having a first end section having a capsule accommodating hole and a second end section having a mouthpiece;
   at least one air flow passage extending axially through the main body so that air flows through the main body when suction is applied through the mouthpiece;
   a pair of pin insertion holes extending laterally through the main body and separated from each other in an axial direction of the main body, the pin insertion holes being formed in the main body to communicate with opposite ends of the capsule accommodating hole and with an inflow-side and an outflow-side of the at least one air flow passage; and
   a perforator having pins adapted for insertion through the respective pin insertion holes to form holes in a capsule when positioned in the capsule accommodating hole.

2. An inhaling type medicine administering device as claimed in claim 1, wherein the at least one air flow passage comprises a pair of air flow passages extending diametrically opposite each other through the main body, each of the air flow passages being in communication with the respective pin insertion holes.

3. An inhaling type medicine administering device as claimed in claim 1, wherein the main body includes an inhaling piece and a capsule holder, the inhaling piece having a first end adapted to detachably receive the capsule holder and a second end serving as the mouthpiece, the capsule holder housing the capsule accommodating hole, the at least one air flow passage extending axially through a wall of the capsule holder, and the pin insertion holes extending laterally through a wall of the inhaling piece and through the capsule holder.

4. An inhaling type medicine administering device as claimed in claim 1, wherein an intermediate portion of the at least one air flow passage between the pin insertion hole at the inflow-side and the pin insertion hole at the outflow-side has a smaller diameter than a remaining portion of the at least one air flow passage.

5. An inhaling type medicine administering device comprising:
   a main body having a first end section having a capsule accommodating hole and a second end section having a mouthpiece;
   an inflow-side air flow passage and an outflow-side air flow passage extending axially in the main body so that air flows through the main body when suction is applied through the mouthpiece;
   a pair of pin insertion holes extending laterally through the main body and separated from each other in an axial direction of the main body, the pin insertion holes being formed in the main body to communicate with opposite ends of the capsule accommodating hole and with the inflow-side air flow passage and the outflow-side air flow passage; and
   a perforator having pins adapted for insertion through the respective pin insertion holes to form holes in a capsule when positioned in the capsule accommodating hole.

6. An inhaling type medicine administering device as claimed in claim 5, wherein the inflow-side air flow passage comprises two inflow-side air passages extending diametrically opposite each other in the main body so as to be in communication with one of the pin insertion holes, and the outflow-side air flow passage comprises two outflow-side air flow passages extending diametrically opposite each other in the main body so as to be in communication with another of the pin insertion holes.

7. An inhaling type medicine administering device as claimed in claim 5, wherein the main body includes an inhaling piece and a capsule holder, the inhaling piece having a first end adapted to detachably receive the capsule holder and a second end serving as the mouthpiece, the capsule holder housing the capsule accommodating hole, the inflow-side air flow passage and the outflow-side air flow passage extending axially in the capsule holder, and the pin insertion holes extending laterally through a wall of the inhaling piece and through the capsule holder.

8. An inhaling type medicine administering device as claimed in claim 3, further comprising at least one auxiliary air flow passage extending axially through the capsule holder and being located at an angle offset 90 degrees relative to the at least one air flow passage.

9. An inhaling type medicine administering device as claimed in claim 3, wherein the capsule holder has an upper wall and a small diameter hole formed through the upper wall of the capsule holder, the small diameter hole being dimensioned for receipt of a needle for pushing out the capsule inside the capsule holder.

10. A method of preparing the inhaling type medicine administering device as claimed in claim 3 for use by a patient, comprising:
    inserting a capsule holder in the first end of the inhaling piece;
    aligning outside pin insertion holes formed in the wall of the inhaling piece with inside pin insertion holes formed in the capsule holder so as to constitute an inflow-side pin insertion hole and an outflow-side insertion hole;
    inserting the pins of the perforator through the inflow-side pin insertion hole and the outflow-side pin insertion hole, respectively, so as to form through-holes in the capsule; and
    drawing out the perforator to a position at which a tip end of each pin of the perforator is positioned in a respective outside pin insertion hole.

11. An inhaling type medicine administering device as claimed in claim 7, further comprising at least one auxiliary air flow passage extending axially through the capsule holder and being located at an angle offset 90 degrees relative to the inflow-side air flow passage and the outflow-side air flow passage.

12. An inhaling type medicine administering device as claimed in claim 7, wherein the capsule holder has an upper wall and a small diameter hole formed through the upper wall of the capsule holder, the small diameter hole being dimensioned for receipt of a needle for pushing out the capsule inside the capsule holder.

13. A method of preparing the inhaling type medicine administering device as claimed in claim 7 for use by a patient, comprising:
    inserting a capsule holder in the first end of the inhaling piece;
    aligning outside pin insertion holes formed in the wall of the inhaling piece with inside pin insertion holes formed in the capsule holder so as to constitute an inflow-side pin insertion hole and an outflow-side insertion hole;
    inserting the pins of the perforator through the inflow-side pin insertion hole and the outflow-side pin insertion hole, respectively, so as to form through-holes in the capsule; and
    drawing out the perforator to a position at which a tip end of each pin of the perforator is positioned in a respective outside pin insertion hole.

* * * * *